United States Patent [19]
Beaty et al.

[11] Patent Number: 5,727,943
[45] Date of Patent: Mar. 17, 1998

[54] SELF-TAPPING, SCREW-TYPE DENTAL IMPLANT

[75] Inventors: Keith D. Beaty, Jupiter; Ralph Goodman; Thomas S. Heylmun, both of West Palm Beach; James W. Reams, Stuart, all of Fla.

[73] Assignee: Implant Innovations, Inc., Palm Beach Gardens, Fla.

[21] Appl. No.: 590,087

[22] Filed: Jan. 24, 1996

Related U.S. Application Data

[60] Provisional application No. 60/001,486, Jul. 18, 1995, and 60/003,359, Sep. 7, 1995.

[51] Int. Cl.⁶ .................................................. A61C 8/00
[52] U.S. Cl. ................................................ 433/174; 606/73
[58] Field of Search ......................... 433/172, 173, 433/174, 175, 176; 606/73, 65; 411/387, 418, 420, 421

[56] References Cited

U.S. PATENT DOCUMENTS

| | | |
|---|---|---|
| 2,093,171 | 9/1937 | Olson . |
| 3,067,740 | 12/1962 | Haboush ................... 128/92 |
| 3,488,779 | 1/1970 | Christensen ................. 3/1 |
| 3,846,846 | 11/1974 | Fischer ..................... 3/1 |
| 3,937,120 | 2/1976 | Munse ..................... 85/47 |
| 3,971,135 | 7/1976 | Leu . |
| 4,104,446 | 8/1978 | Johnson ................... 428/585 |
| 4,145,764 | 3/1979 | Suzuki et al. ............... 3/1.9 |
| 4,324,550 | 4/1982 | Reuther et al. ............ 433/174 |
| 4,406,623 | 9/1983 | Grafelmann et al. ......... 433/174 |
| 4,414,966 | 11/1983 | Stednitz .................. 128/92 B |
| 4,463,753 | 8/1984 | Gustilo .................. 128/92 B |
| 4,468,200 | 8/1984 | Münch .................... 433/174 |
| 4,480,997 | 11/1984 | Deutsch et al. ............ 433/221 |
| 4,484,570 | 11/1984 | Sutter et al. ............. 128/92 D |
| 4,495,664 | 1/1985 | Blanquaert ............... 3/1.913 |
| 4,511,335 | 4/1985 | Tatum, Jr. ................ 433/173 |
| 4,535,487 | 8/1985 | Esper et al. ............... 623/22 |
| 4,537,185 | 8/1985 | Stednitz .................. 128/92 B |
| 4,583,898 | 4/1986 | Sygnator .................. 411/387 |
| 4,713,004 | 12/1987 | Linkow et al. ............. 433/174 |
| 4,722,688 | 2/1988 | Lonca ..................... 433/173 |
| 4,738,623 | 4/1988 | Driskell .................. 433/173 |

(List continued on next page.)

FOREIGN PATENT DOCUMENTS

| | | |
|---|---|---|
| 0 111134 | 6/1984 | European Pat. Off. . |
| 0 126624 | 11/1984 | European Pat. Off. . |
| 0 139052 | 5/1985 | European Pat. Off. . |
| 0237505 | 9/1987 | European Pat. Off. . |
| 0 288702 | 11/1988 | European Pat. Off. . |
| 0 501940 | 9/1992 | European Pat. Off. . |
| 0 530160 | 3/1993 | European Pat. Off. . |
| 3043336 | 11/1981 | Germany . |
| 332486 | 2/1971 | Sweden . |
| 1 291 470 | 10/1972 | United Kingdom . |
| WO 95/17135 | 6/1995 | WIPO . |

OTHER PUBLICATIONS

Machinery's Handbook (1979, pp. 1686–1689).
Fundamentals of Tool Design, 2nd Edition by Harp, et al (1984 pp. 124–126).
The Ha-Ti Implant, Lederman, Frischherz, and Markwalder (1991, pp. 611–615).
Bioceram's Single Crystal Sapphire and Ceramic Dental Implants by Kyocera.
Bone Stew Technical Information by Richards Technical Publication (1980, pp. 1–14).

*Primary Examiner*—Cary E. O'Connor
*Attorney, Agent, or Firm*—Arnold, White & Durkee

[57] ABSTRACT

A self-tapping dental implant comprises a generally cylindrical body with a threaded outer surface for securing the implant to the walls of a preformed hole in a jaw bone. The cylindrical body has a plurality of longitudinal recesses formed in the threaded surface at one end and extends longitudinally through a plurality of turns of the thread to form a self-tapping cutting edge at each interruption of the thread by one of the recesses. Each thread segment extends between a pair of adjacent recesses and diminishes in radius between the leading and trailing ends of the thread segment.

72 Claims, 9 Drawing Sheets

U.S. PATENT DOCUMENTS

| | | | |
|---|---|---|---|
| 4,787,792 | 11/1988 | Jenson et al. | 411/387 |
| 4,826,434 | 5/1989 | Krueger | 433/174 |
| 4,851,008 | 7/1989 | Johnson | 623/16 |
| 4,878,915 | 11/1989 | Brantigan | 623/17 |
| 4,932,868 | 6/1990 | Linkow et al. | 433/174 |
| 4,978,350 | 12/1990 | Wagenknecht | 606/72 |
| 4,988,299 | 1/1991 | Branemark | 433/174 |
| 5,000,639 | 3/1991 | Hinkley et al. | 411/418 |
| 5,064,425 | 11/1991 | Brånemark et al. | 606/72 |
| 5,269,685 | 12/1993 | Jörnéus et al. | 433/174 |
| 5,427,527 | 6/1995 | Niznick et al. | 433/174 |
| 5,435,723 | 7/1995 | O'Brien | 433/174 |
| 5,549,677 | 8/1996 | Durr et al. | 433/174 |

5,727,943

1

SELF-TAPPING, SCREW-TYPE DENTAL IMPLANT

REFERENCE TO PRIOR PROVISIONAL APPLICATIONS

This application claims the benefit of copending provisional application Ser. No. 60/001,486, filed Jul. 18, 1995, entitled: "Self-Tapping Dental Implant", and copending provisional application Ser. No. 60/003,359, filed Sep. 7, 1995 and entitled: "Super Self-Tapping Dental Implant."

FIELD OF THE INVENTION

The present invention relates generally to dental implants and, more particularly, to screw-type dental implants which are self-tapping.

BACKGROUND OF THE INVENTION

Screw-type dental implants are widely used and have been known for a number of years. A self-tapping dental implant is one that can be threaded into a pre-drilled hole in a jaw bone without pre-tapping the hole. The apical end portion of the implant itself taps the hole as the implant is simultaneously pressed into the hole and rotated.

Self-tapping implants have been well known for a number of years, but they are generally more difficult to install than non-self-tapping implants which require pre-tapping of the hole. One problem with self-tapping implants is the instability of the implant when it is first inserted into the pre-drilled hole; this instability can make it difficult to ensure that the axis of the implant is aligned with, and parallel to, the axis of the hole. Another problem particularly with hard jaw bones, is the amount of torque that must be manually applied to the implant to overcome the friction between the implant and the bone to effect self-tapping of the implant into the bone. There has been an ongoing need for a self-tapping implant that would alleviate these problems.

SUMMARY OF THE INVENTION

It is a primary object of the invention to provide an improved self-tapping dental implant that stabilizes itself at the beginning of the self-tapping operation so that the axis of the implant is coaxially aligned with the pre-drilled hole in the jaw bone.

Another important object of the invention is to provide an improved self-tapping dental implant that reduces the torque required to be applied to the implant during the self-tapping operation, by reducing the friction between the implant and the bone. A related object is to reduce the time required to install the implant.

A further object of the invention is to provide such an improved self-tapping dental implant having highly efficient bone-cutting surfaces in the self-tapping region of the implant.

Other objects and advantages of the invention will become apparent from the following detailed description and the accompanying drawings.

In accordance with the present invention, the foregoing objectives are realized by providing an improved self-tapping dental implant comprising a generally cylindrical body having a threaded outer surface for securing the implant to the walls of a preformed hole in a jaw bone, and a plurality of longitudinal recesses formed in the threaded surface at one end thereof and extending longitudinally

2 through a plurality of turns of the thread to form a self-tapping cutting edge at each interruption of the thread by one of the recesses. In one aspect of the invention, each thread segment that extends between a pair of adjacent recesses diminishes in radius between the leading and trailing ends of the thread segments. In another aspect of the invention, the threaded surface of the implant body is tapered in the longitudinal direction along at least a portion of the recesses so that successive cutting edges along the thread in the tapered region have progressively changing radii, decreasing toward the smaller end of the implant.

DETAILED DESCRIPTION OF PREFERRED EMBODIMENTS

Figure 2:
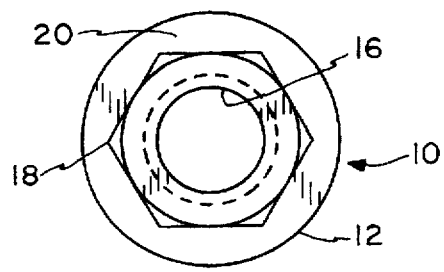
FIG. 2 is a top plan view of the implant of FIG. 1.

While the invention is susceptible to various modifications and alternative forms, specific embodiments thereof have been shown by way of example in the drawings and will be described in detail herein. It should be understood, however, that it is not intended to limit the invention to the particular forms disclosed, but, to the contrary, the intention is to cover all modifications, equivalents and alternatives falling within the spirit and scope of the invention as defined by the appended claims.

Figure 1:
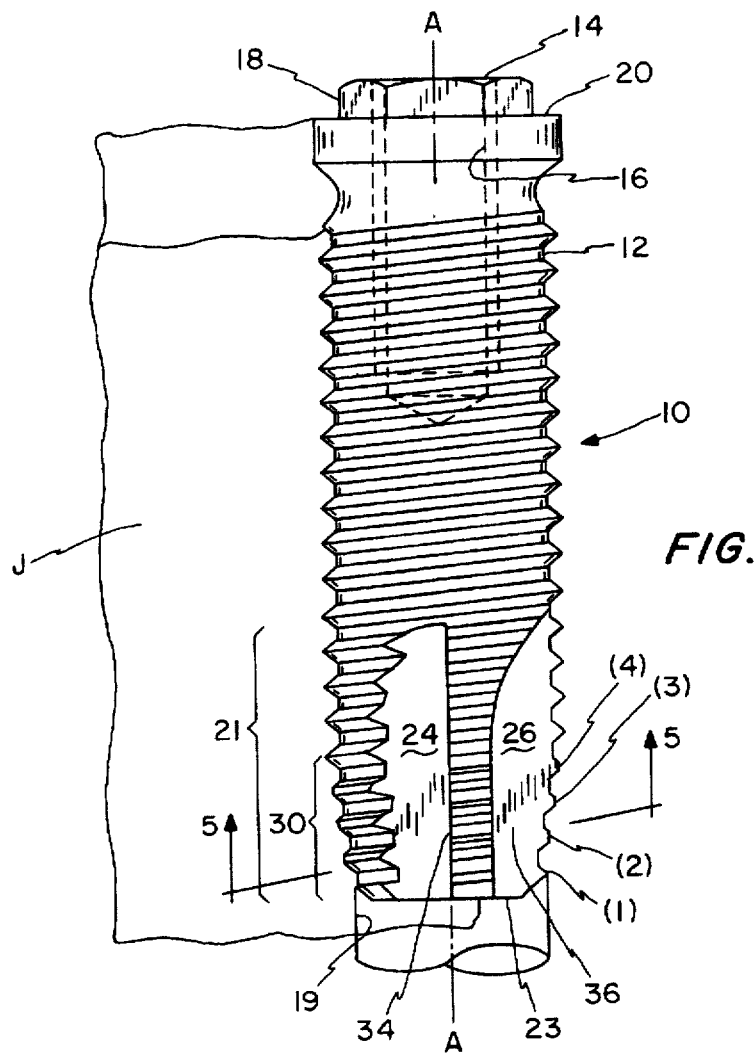
FIG. 1 is a side elevation of a dental implant embodying the present invention.
Figure 3:
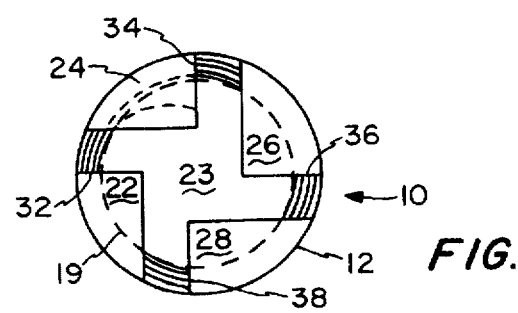
FIG. 3 is a bottom plan view of the implant of FIG. 1.

Turning now to the drawings and referring first to FIGS. 1–3, a dental implant has an externally threaded, substantially cylindrical main body 12 symmetrical around the longitudinal axis A—A of the implant. The top end 14 of the implant 10 is fitted in a known way for receiving dental components useful for making a dental restoration, as well as a dental restoration itself. As can be seen in FIG. 2, the illustrative implant 10 has an internal bore 16 which is internally threaded for receiving a machine-screw-like bolt (not shown) and, surrounding this bore, a hexagonal boss 18 which can be engaged for screwing the implant into a pre-drilled bore 19 in a patient's jaw bone J. The hexagonal boss 18 also forms part of a non-rotational coupling between the implant 10 and the above-mentioned components and restoration. The boss 18 is surrounded by an annular shoulder 20 against which such components and restoration may abut when attached to the implant 10.

The bottom end 21 of the implant 10 has four axially elongated recesses or cut-outs 22, 24, 26 and 28, spaced symmetrically 90 degrees apart around the longitudinal axis of the implant 10. These four recesses form four cutting edges 32, 34, 36 and 38 which are effective to self-tap the implant 10 into the pre-drilled bore 19 when the implant 10 is turned counterclockwise around the longitudinal axis as viewed in FIG. 4 (in the direction indicated by the curved arrow B).

Figure 4:
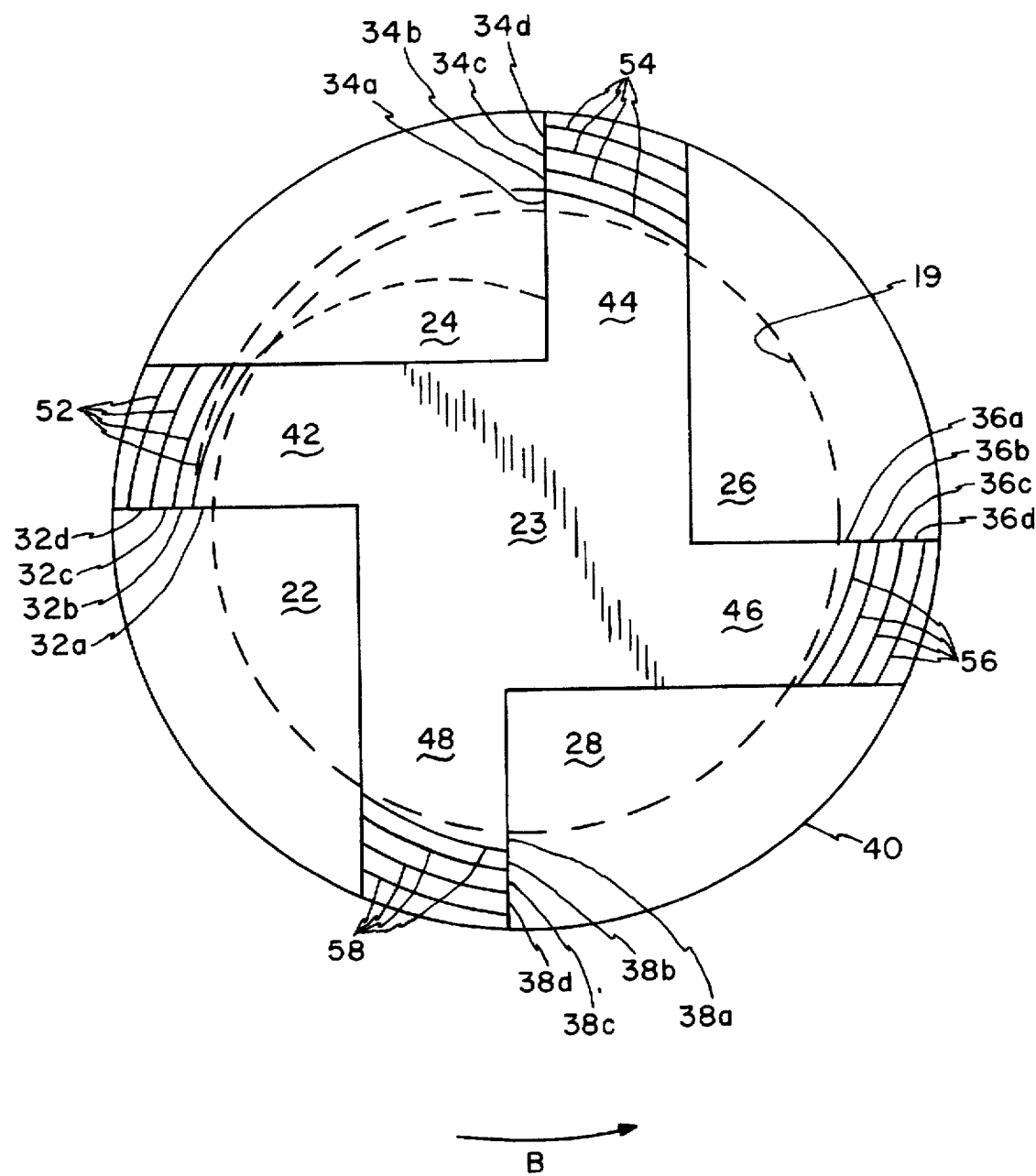
FIG. 4 is an enlarged version of FIG. 3 showing the incremental self-tapping cutting action of the invention starting at the bottom end of the implant.

As seen most clearly in the enlarged FIG. 4, the cutting edges 32, 34, 36 and 38 are all within the circular locus 40 of the main body 12, so that the threads on the main body following the self-tapping threads into the bore 19 will engage in the side wall of the bore 19 and thereby prevent wobbling of the implant 10 as it is screwed into the patient's jaw bone J. The main body portions 42, 44, 46 and 48 that remain between adjacent pairs of the recesses 22-28 have elongated circumferential thread segments 52, 54, 56 and 58, respectively. These thread segments are actually milling tools in that they are used to cut internal threads into the preformed bore of the bone. As such, thread segments 52, 54, 56, and 58 are actually modified thread segments because of the additional function they perform. If these modified thread segments had constant major and minor radii, they could rub on the interior wall of the bore 19 as the implant 10 is threaded into that bore 19. To reduce such rubbing friction between the segments 52-58 and the jaw bone J, the major and minor radial dimensions of each of these segments are progressively reduced substantially immediately following the relevant cutting edge, and this reduction continues to the trailing edge of the segment.

For example, looking at the body portion 42, the major radius of each segment 52 is progressively reduced in size from the recess 22 to the recess 24 so that the outer surface of this segment takes on an inwardly-curving contour. FIG. 4 shows a set of such contours, on successively smaller diameters proceeding toward the bottom end of the implant 10, due to the fact that the bottommost portion 30 of the self-tapping segment of the implant tapers to a smaller size toward the extremity 23 of the bottom end 21. Accordingly, each tapping thread segment, regardless of the diameter of its circumferential locus, is provided with this friction-reducing structure. As illustrated by the innermost broken-line arc in FIG. 4, the major radius of curvature of each thread segment is smaller than that of the implant body 12 and the bore hole 19.

As can be seen in FIG. 4, this configuration confines the engagement between the peak of the self-tapping thread and the bone to the cutting edges of the tapping thread segments. Thus, the torque applied to the implant 10 to thread it into the bone is utilized primarily to cut a thread into the bone, and not to overcome friction between the bone and non-cutting major diameter surfaces of the implant. Consequently, the torque required to be applied to the implant 10 to effect self-tapping is reduced, as is the time required to install the implant 10.

Figure 5:
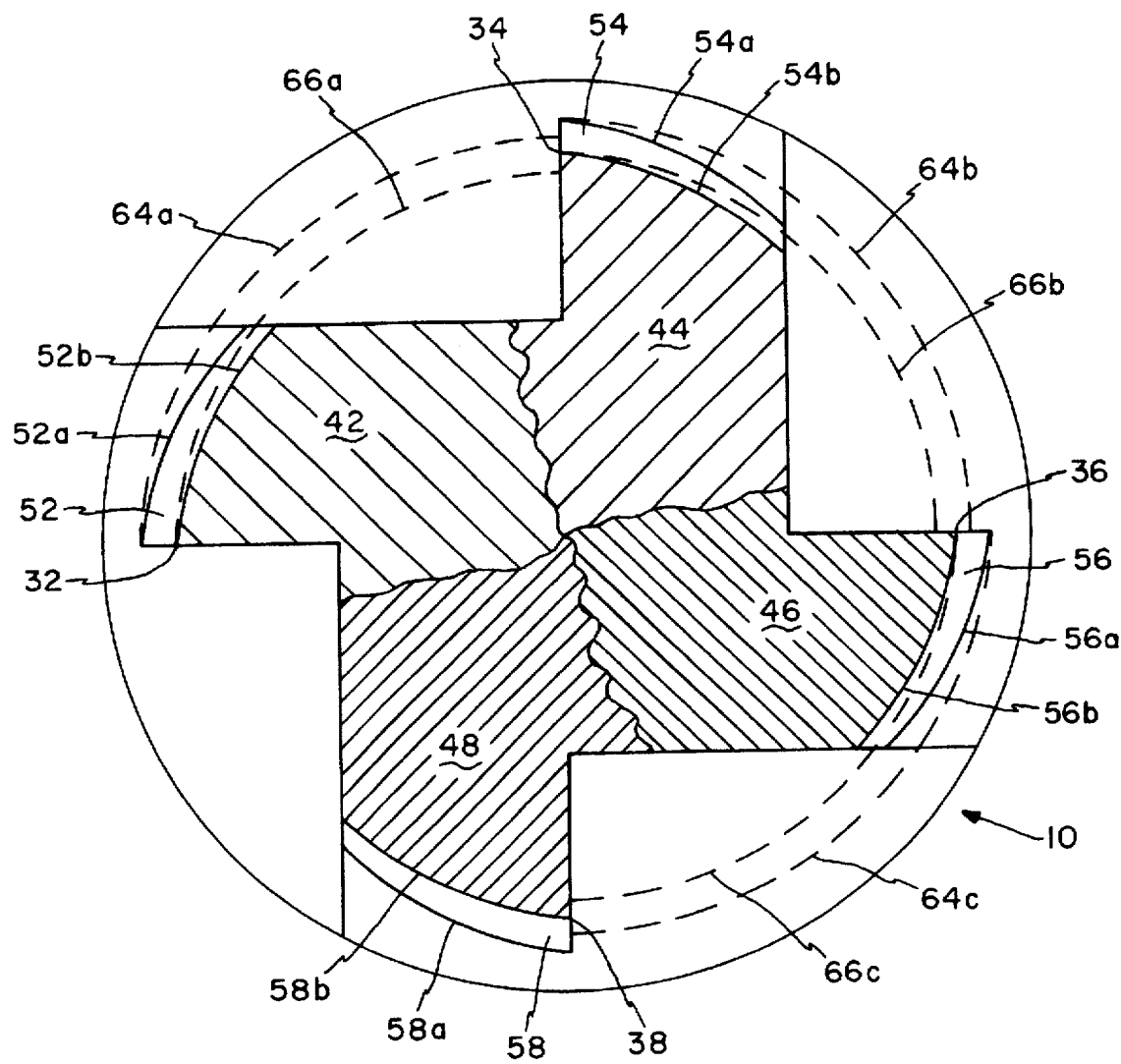
FIG. 5 is a helical section view taken along line 5—5 in FIG. 1 showing four successive thread segments.

FIG. 5 is a helical section view of the implant 10 showing the peaks and the troughs of four successive thread segments 52, 54, 56 and 58 corresponding to one thread turn, and their associated four body portions 42, 44, 46 and 48. In FIG. 5, the reference numerals 52a, 54a, 56a and 58a indicate the peak, or major diameter, of the thread segments following the respective relevant cutting edges 32, 34, 36 and 38. Reference numerals 52b, 54b, 56b and 58b indicate the trough, or minor diameter, of each of those respective thread segments. In accordance with the invention, the troughs 52b, 54b, 56b and 58b, as well as the peaks 52a, 54a, 56a and 58a, of these thread segments move toward the implant axis thereby reducing the minor diameter as well as the major diameter of each segment, immediately following the relevant cutting edge. The circular dashed line 64a shows the cutting locus of the peak of the cutting edge 32, while the circular dashed line 66a of relatively smaller radius shows the cutting locus of the trough of the same cutting edge 32. As is evident from these locus lines, both the peak 52a and the trough 52b of the thread segment 52 are "friction relieved" away from the interior of the bore immediately following the cutting action of the cutting edge 32.

Similarly the peak 54a and the trough 54b of the thread segment 54 are "friction relieved" away from the interior of the bore immediately following the cutting action of the cutting edge 34, as is apparent from the major and minor locus lines 64b and 66b. It is also apparent from the major and minor locus lines 64b and 66b of the second cutting edge 34 are larger than the major and minor radii 64a and 66a of the first cutting edge 32. The third thread segment 56 includes a peak 56a and trough 56b with still larger radii and its cutting edge 36 cuts on these larger radii as is indicated by the major and minor locus lines 64c and 66c. Thread segment 56 is similarly "friction relieved" at both its peak 56a and its trough 56b The fourth thread segment 58 shown in FIG. 5 has similar properties, as do the thread segments of successive thread turns which follow on increasingly larger radii in the bottom end 21 of the implant 10. It should be noted that the amount of reduction in the major radius is independent of the reduction in the minor radii. Thus, the major radii may be reduced more or less than the minor radii.

Although the frictional relief is shown starting immediately after the cutting edges, the frictional relief may also start a short distance behind the cutting edge. Furthermore, the relief may be accomplished by other methods than by reducing the major and minor radii. For example, the reduction in the pitch radius which has been discussed thus far is typically measured from the longitudinal axis of the body of the implant. After the cutting edge, the major and minor radii measured from the longitudinal axis are reduced. However, if the axis from which the radius is measured is offset from the longitudinal axis, then relief may accomplished in this manner as well. In this way, the radius after the cutting edge is not reduced, but instead is merely measured from an axis offset from the longitudinal axis of the implant to achieve the desired relief.

Figure 6:
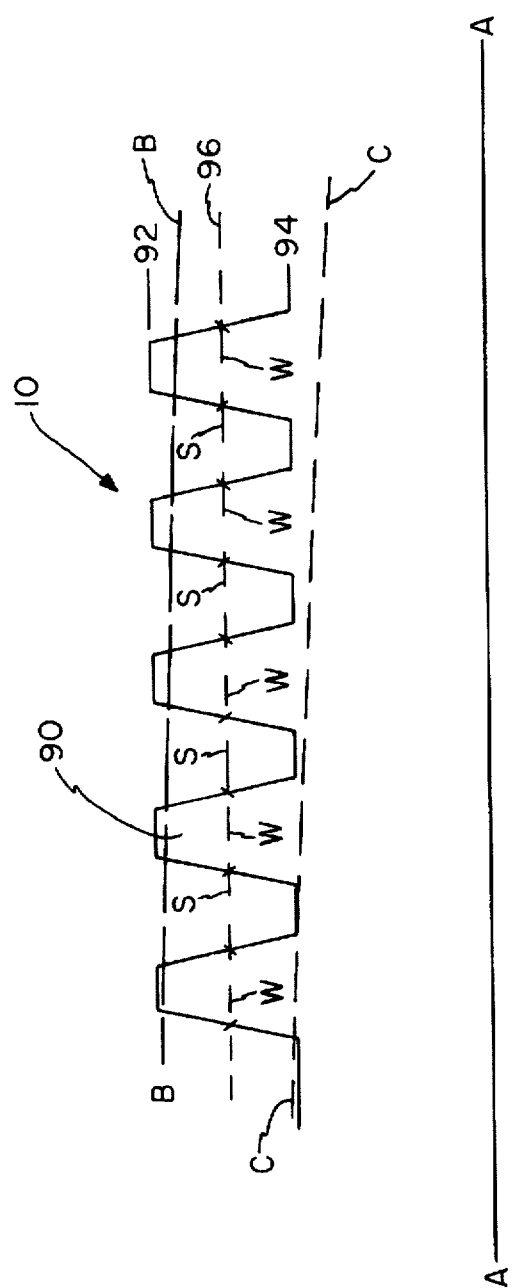
FIG. 6 is a section view of the threads of the implant illustrating the major, minor, and pitch diameter.

The invention may be further understood with the aid of FIG. 6, illustrating the implant 10 with an external thread 90 having a major radius 92 and a minor radius 94. The line A—A represents the longitudinal axis of the implant 10. By definition, the "pitch radius" of the thread 90 is located on the line 96 on which the thread width W of each turn is equal to the space S between adjacent turns. This property is not affected by changing the major radius 92 alone, as is indicated by the sloped line B—B, which shows a progressive reduction of the major radius from one thread turn to the next. On the other hand, if both the major radius 92 and minor radius 94 of the thread 90 are reduced together, no other change in the thread parameters being made, the pitch radius 96 is also reduced as can be seen if the minor radius is reduced along line C—C. Thus, as is shown in FIGS. 1 and 4, the bottom portion 30 of the implant 10 tapers to a smaller size toward the extremity 23 in a shape which reduces both the major and the minor radii of the thread, thereby reducing the pitch radius as well. Referring again to FIG. 5, the progressive reduction of both the major and the minor radii of each thread segment 52, 54, 46 and 58 brings about a progressive reduction of the pitch radius of that thread segment. Consequently, in the illustrated embodiment, the pitch radius of each thread segment is gradually reduced from the cutting edge to the trailing edge of that thread segment.

As can be seen most clearly in FIG. 1, the lower portion 30 of the implant 10 is tapered to a smaller diameter than the main body 12 over an axial distance encompassing at least the last four thread turns, which are numbered (1), (2), (3) and (4), respectively, beginning at the apical end surface 23. In order to maintain a substantially constant thread depth along the length of the tapered portion 30, both the minor and major radii of the thread (from the axis of the implant) increase progressively between the narrow end and the wide end of the tapered portion 30 (see FIGS. 1 and 4). As can be seen in FIG. 1, the bore 19 has an internal radius which is smaller than the major (outer) radius of the first thread turn (1). The first thread turn (1) therefore starts cutting into the sidewalls of the bore 19 immediately upon introduction of the implant 10 into the bore by rotating the implant about its axis while pressing it axially into the bore. As the implant 10 is advanced into the bore 19, the successive cutting edges 32a, 34a, 36a and 38a formed along the first turn (1) of the thread cut progressively deeper into the bore wall. The depth of the cut made by the first cutting edge 32a is illustrated by the broken line emerging from the tip of that cutting edge in FIG. 4.

As can be seen in FIG. 4, because of the taper of the lower portion 30 of the implant 10, each of the cutting edges 32b, 34b, 36b and 38b in the second turn (2) of the implant thread has a larger radius than the corresponding cutting edge in the first turn (1). Similarly, the cutting edges 32c–38c in the third turn (3) and edges 32d–38d in the fourth turn (4) all progressively increase in radius so that they cut progressively deeper into the bore wall as the implant 10 is threaded into the bore 19.

Figure 7:
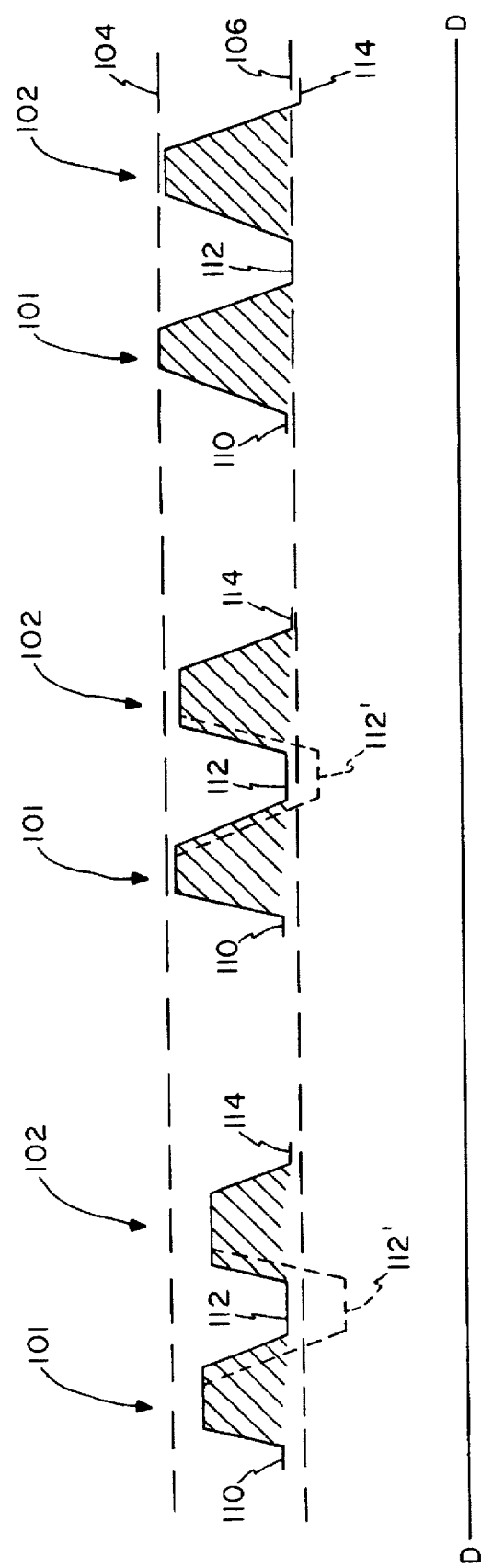
FIGS. 7A–7C are section views of a trough between two longitudinally adjacent thread segments along the tapered, lower portion of the implant.

FIGS. 7A–7C illustrate three sectional cuts through two longitudinally adjacent modified thread segments 101 and 102 in the tapered end of the implant. FIG. 7A is a sectional view immediately behind the cutting edge of the modified thread segments 101 and 102. FIG. 7B is a sectional view between the cutting edge and the trailing end of the thread segments 101 and 102. FIG. 7C is a sectional view near the trailing end of the thread segments 101 and 102. In essence, FIGS. 7A–7C progressively show the thread segments 101 and 102 at different circumferential locations from a point near their cutting edges to a point near their trailing ends.

Line D—D represents the longitudinal axis of the implant. Line 104 is the major radius of thread segment 101 immediately following its cutting edge. Line 106 is the minor radius of thread segment 101 immediately following its cutting edge. Line 106 coincides with the radius of trough 112.

Thread segment 102 is closer to the apical end of the implant than thread segment 101. This is shown by the relative radii of troughs 110, 112, 114 with respect to longitudinal axis D—D. Trough 114 has the smallest radius while trough 110 has the largest radius with the radius of trough 112 falling therebetween. This is also shown by the relative radii of the peaks of thread segments 101 and 102.

The dashed lines represent the current invention. As can be seen by the solid-line trough 112, the radius of the floor of the trough 112 progressively increases due to the fact that each thread segment in the tapered portion is spiraling outward away from the longitudinal axis D—D of the implant so as to eventually merge with the threads in the non-tapered body of the implant which typically have larger major and minor radii. The present invention offsets this rising floor of the trough 112 by cutting further into the implant body to produce trough 112' shown in dashed lines in FIGS. 7B–7C. This cutting produces additional relief and effectively modifies the pitch radius such that it remains constant or even decreases in the tapered end portion. Thus, as bone tissue is initially cut by the cutting edge of the present invention, it does not continuously encounter a progressively rising trough 112 which would then compact the bone into the sidewalls of the bore of the bone. Instead, it encounters reduced-radius trough 112'. Continuous compression of the bone tissue can lead to trauma of that bone tissue. The present invention minimizes the likelihood of such trauma.

Moreover, as an implant lacking the inventive reduction in minor radius is turned into the bore, bone tissue entering trough 112 between the two longitudinally adjacent thread segments 101 and 102 would confront not only a rising floor due to the normally increasing minor radius associated with the taper, but it also would encounter a reduced area through which it must pass. On the other hand, as the minor radius decreases to produce trough 112', the tool which cuts the progressively deeper trough 112' extends further inward toward the longitudinal axis D—D. Consequently, the sides of the thread segments 101 and 102 are also cut by the tool to produce additional area between two longitudinally adjacent thread segments 101 and 102 as is shown by the dashed lines. Thus, the area between the two longitudinally adjacent threads segments 101 and 102 increases as does the volume therebetween. This increase allows for the bone tissue to adequately occupy this volume, but not so much so that the bone tissue is compressed to a point at which trauma may occur. In the preferred embodiment of this invention, the minor radius at trough 112' decreases in a manner to at least offset the reduction in area due to the normal increasing minor radius associated with the tapering at the lower portion of the implant.

In each thread turn the four cutting edges 32, 34, 36, 38 are equally spaced around the longitudinal axis of the implant 10, which contributes to axial stability from the start of the threading of the implant 10 into the bore 19. To further contribute to such stability, each succeeding cut increases the depth by only a small increment (typically 0.001 inch), which correspondingly restrains the increase of friction to small incremental increases. The initial cut made by the first cutting surface to engage the bone (cutting surface 32a in the implant of FIGS. 1–4) is slightly deeper than the incremental increase in the cutting depth effected by each successive cutting surface. By the time the entire tapered portion 30 has entered the bore 19, the path of the implant 10 into the bore is stably established.

It should be noted that the successive increases in the cutting radius occur not only in the first thread turn, but also in each successive thread turn. Thus, in the illustrative implant 10 in which the taper extends over four thread turns, and in which the four recesses provide four incremental increases in the cutting radius in each thread turn, there are a total of 16 incremental increases in the cutting radius along the entire length of the taper.

Of course, the tapered portion of the implant 10 may extend over any desired number of thread turns, either greater or fewer than the four-thread turns in the tapered region of the implant of FIGS. 1-4. Also, the thread itself may be either a right-hand thread or a left-hand thread, and may be either a single-lead thread (as illustrated) or a multiple-lead thread.

Figure 8:
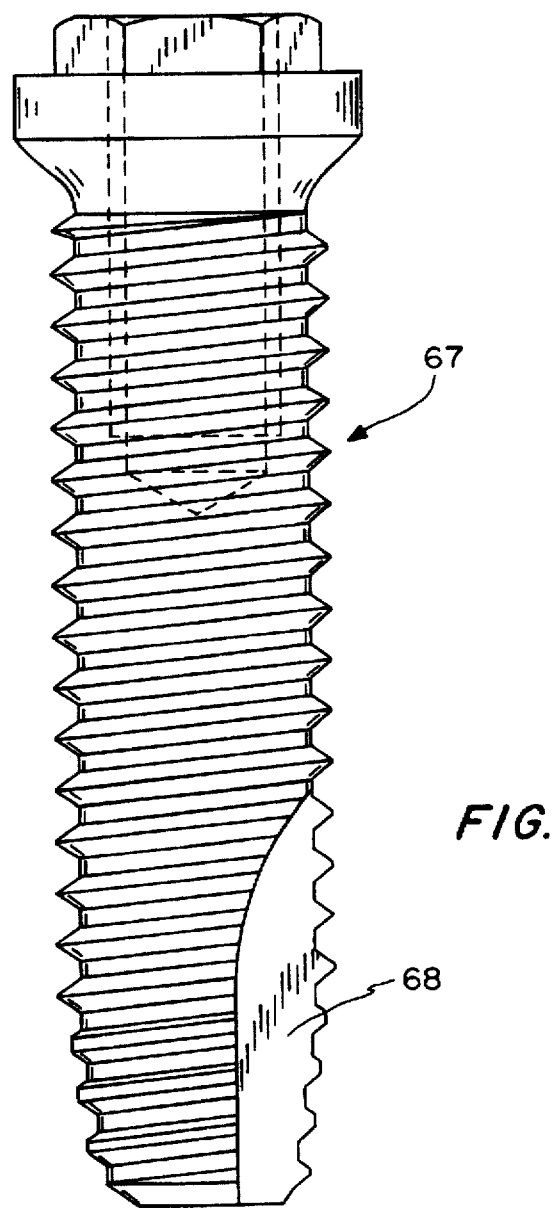
FIG. 8 is a side elevation of a small-diameter dental implant embodying the invention.
Figure 9:
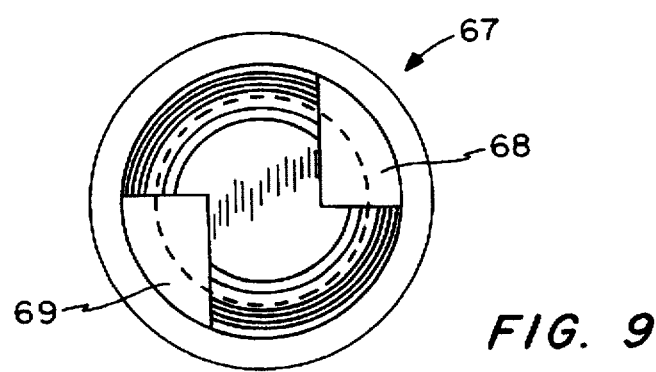
FIG. 9 is a bottom plan view of the implant of FIG. 8.
Figure 10:
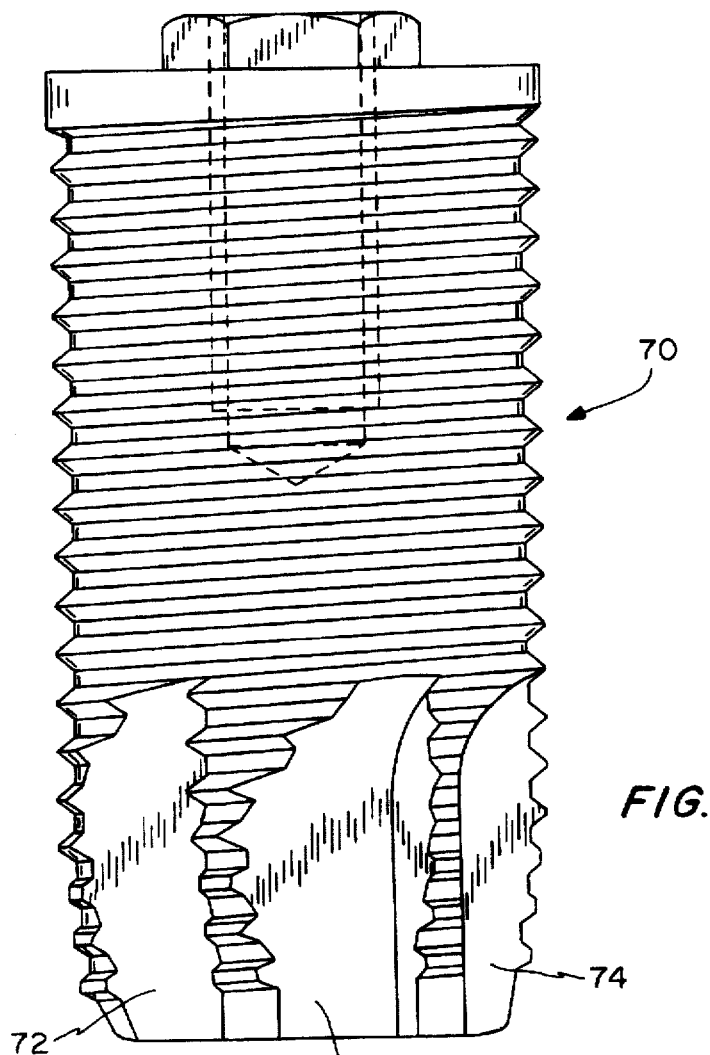
FIG. 10 is a side elevation of a large-diameter dental implant embodying the invention.
Figure 11:
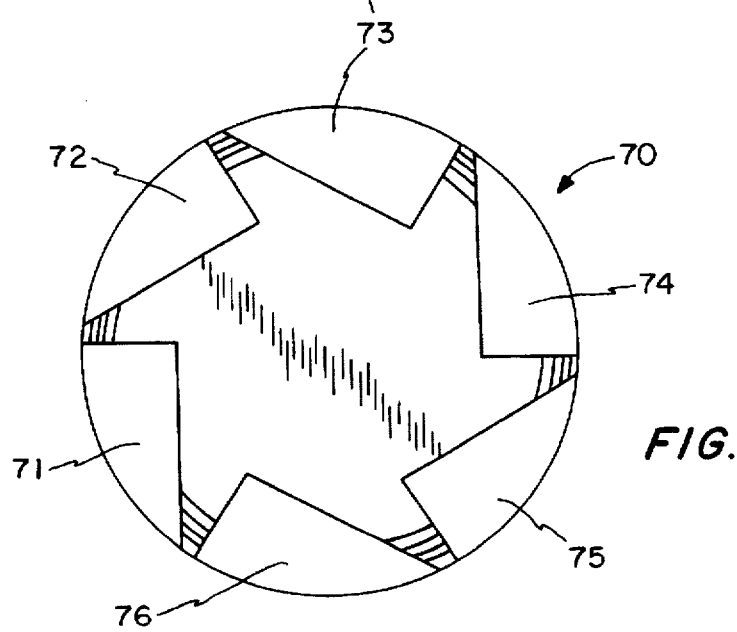
FIG. 11 is a bottom plan view of the implant of FIG. 10.

It will also be appreciated that the number of recesses included in the implant may be greater or fewer than the four recesses included in the implant of FIGS. 1-4. For example, FIGS. 8 and 9 illustrate a narrow implant 67 that has only two recesses 68 and 69, diametrically opposed, because of the smaller diameter of the implant. FIGS. 10 and 11 illustrate a wide implant 70 that includes six recesses 71-76 equally spaced around the axis of the implant, because of the larger diameter of the implant.

Figure 12:
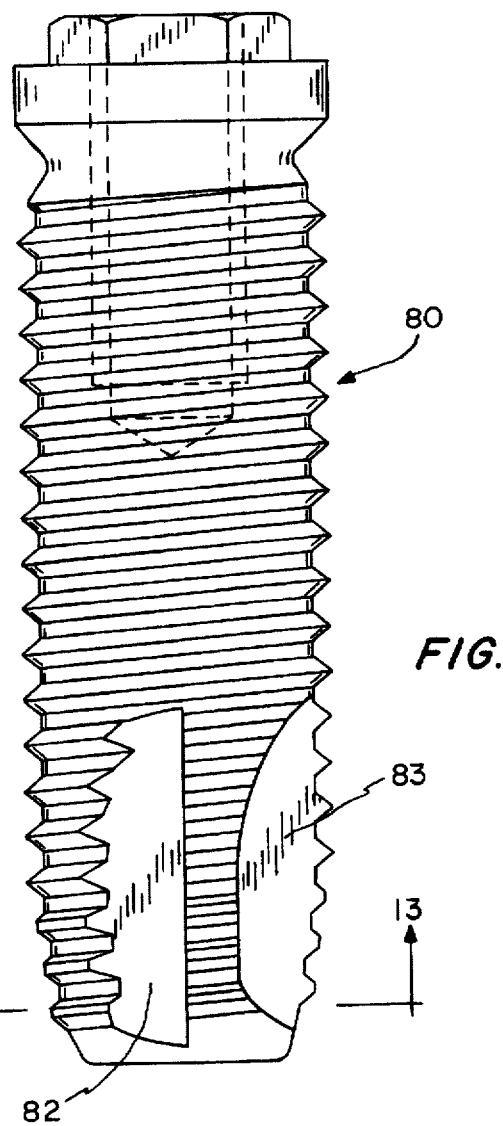
FIG. 12 is a side elevation of a modified implant embodying the invention.
Figure 13:
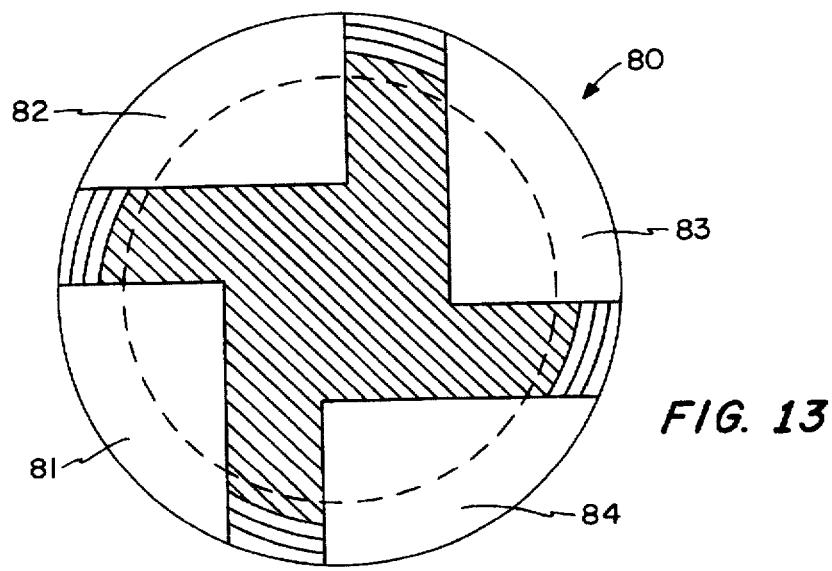
FIG. 13 is a section taken generally along line 13—13 in FIG. 12.

FIGS. 12 and 13 illustrate an implant 80 in which the recesses 81-84 are at least partially closed at both ends rather than extending through to the apical end of the implant as in the implant 10 of FIGS. 1-6. The closed-end recesses 81-84 direct the bone particles from the tapping operation to the side wall of the pre-drilled hole rather than to the end of the hole, to perhaps facilitate bonding of the bone to the implant 80.

Figure 14:
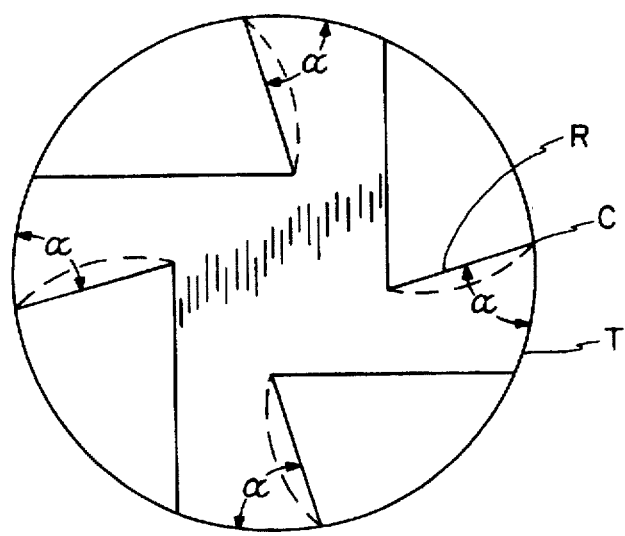
FIG. 14 is a diagrammatic side elevation of the bottom portion of a dental implant embodying a modified version of the invention.

Although the cutting surface formed by each of the recesses described above lies in a radial plane extending parallel to the axis of the implant, the plane of the cutting surfaces may be tilted as illustrated in the FIG. 14 to form an acute angle α in transverse cross-section, forming a chisel-like corner C at the outermost edge of the cutting surface. That is, the recess wall R that forms the cutting edge forms an acute angle α with the thread segment T that trails that cutting edge. This acute angle α concentrates the force applied to the bone during the self-tapping operation in a smaller area of the bone, thereby reducing the amount of torque required to be applied to the implant to effect self-tapping.

Figure 15:
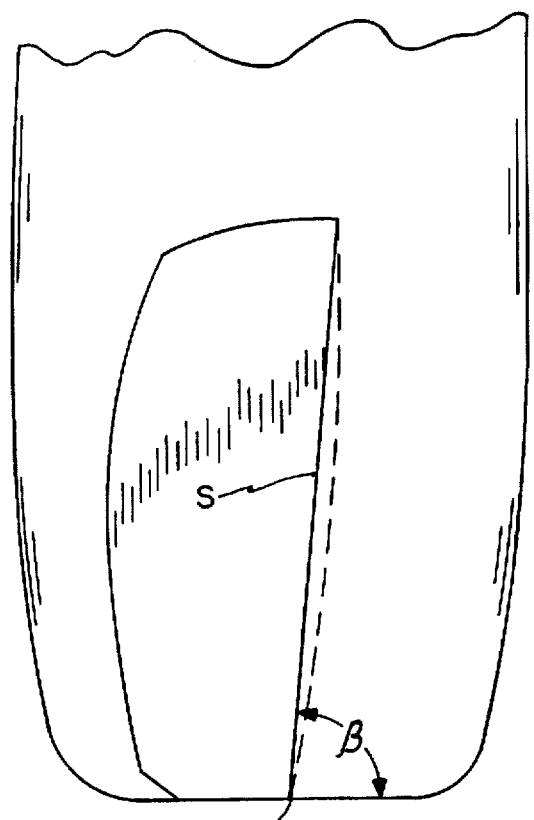
FIG. 15 is a diagrammatic bottom plan view of a dental implant embodying another modified version of the invention.

To concentrate the applied force in an even smaller area of the bone, the plane of the cutting surface S may also be tilted as illustrated in FIG. 15 to form an acute angle β in longitudinal cross-section or side elevation, forming a sharp point P at the distal end of the outermost edge of the cutting surface. If desired, the cutting surface may be made curvilinear in either or both of the transverse and longitudinal sections, as illustrated by the broken lines in FIGS. 14 and 15, to even further concentrate the force applied to the bone by the implant during self-tapping.

We claim:

1. A self-tapping implant for installation in living bone and to which a prosthesis is to be coupled, comprising:
   a generally cylindrical body having an apical end, a gingival end and a threaded outer surface between said ends for securing said implant to the walls of a preformed hole in said living bone, said threaded outer surface tapering inwardly toward a longitudinal axis of the cylindrical body at the apical end of the body, said gingival end of said body including means for coupling said body to said prosthesis,
   said body having a plurality of longitudinal recesses formed in said threaded surface at said apical end and extending through a plurality of thread turns of progressively diminishing radii toward said apical end, said plurality of longitudinal recesses forming a sequence of self-tapping cutting edges one of which being located at each interruption of the thread by one of said recesses, the thread-peaks at said cutting edges moving progressively closer to said axis when proceeding along the thread toward said apical end, and
   each modified thread segment that extends between adjacent ones of said plurality of recesses having a major and minor radii, said major and minor radii diminishing around said axis between the leading and trailing ends of said modified thread segment.

2. A self-tapping implant for installation in living bone comprising:
   a generally cylindrical body having a threaded outer surface for securing the implant to the walls of a preformed hole in said living bone,
   said body having a plurality of longitudinal recesses formed in said threaded surface at one end thereof and extending longitudinally through a plurality of turns of the thread to form a self-tapping cutting edge at each interruption of the thread by one of said recesses,
   the threaded surface of said body being tapered in a longitudinal direction along at least a portion of said recesses so that successive cutting edges along the thread in the tapered region have progressively changing radii, and
   each modified thread segment that extends between adjacent ones of said plurality of recesses having a pitch radius, said pitch radius diminishing around a longitudinal axis of said implant between the leading and trailing ends of the modified thread segment.

3. The self-tapping implant of claim 2 wherein the tapered portion of said threaded surface is located at an end of the implant so that the minimum diameter of the implant is at the end of the implant, and the radii of successive cutting edges along the thread progressively increase as the thread extends away from the end of the implant.

4. The self-tapping implant of claim 2 wherein each modified thread segment extending between a pair of adjacent recesses diminishes in its major and minor radii between the leading and trailing ends of the modified thread segment.

5. The self-tapping implant of claim 2 wherein each of said plurality of recesses extends in a direction parallel to said longitudinal axis of the implant.

6. The self-tapping implant of claim 2 wherein said pitch radii diminish immediately behind said cutting edges.

7. The self-tapping implant of claim 2 wherein each of said plurality of recesses extends through one end of the implant.

8. The self-tapping implant of claim 2 wherein the radius of curvature of each of said modified thread segments is smaller than the radius of curvature of the wall of said preformed hole in the bone.

9. The self-tapping implant of claim 2 which is made of titanium.

10. The self-tapping implant of claim 2 wherein said body further includes means for coupling a prosthesis thereto.

11. The self-tapping implant of claim 10 wherein said coupling means includes an internal bone in said body.

12. The self-tapping implant of claim 10 wherein said coupling means is located at an end opposite said one end.

13. A self-tapping implant for installation in living bone and to which a prosthesis is to be coupled, comprising:
   a generally cylindrical body having a threaded outer surface for securing the implant to the walls of a preformed hole in said living bone,
   said body having a plurality of longitudinal recesses formed in said threaded surface at one end thereof and extending longitudinally through a plurality of turns of the thread to form a self-tapping cutting edge at each interruption of the thread by one of said recesses, the threaded surface of said body being tapered in the longitudinal direction along at least a portion of said recesses so that successive cutting edges along the thread in the tapered region having progressively changing radii, said body including means for coupling said prosthesis thereto, and each modified thread segment extending between a pair of adjacent recesses diminishes in pitch radius between the leading and trailing ends of the modified thread segment.

14. The self-tapping implant of claim 13 wherein both the troughs defining the minor radii and the peaks defining the major radii of the modified thread segments taper in the longitudinal direction so as to define said longitudinal taper of said threaded surface.

15. The self-tapping implant of claim 13 wherein said pitch radii diminish immediately behind said cutting edges.

16. The self-tapping implant of claim 13 wherein each of said recesses extends through one end of the implant.

17. The self-tapping implant of claim 13 wherein the radius of curvature of each of said modified thread segments is smaller than the radius of curvature of the wall of said preformed hole in the bone.

18. A self-tapping implant for installation in living bone comprising a generally cylindrical body having a threaded outer surface for securing the implant to the walls of a preformed hole in said living bone, said body having a plurality of longitudinal recesses formed in said threaded surface at one end thereof and extending longitudinally through a plurality of turns of the thread to form a self-tapping cutting edge at each interruption of the thread by one of said recesses, and each modified thread segment extending between a pair of adjacent recesses diminishing in pitch radius between the leading and trailing ends of the modified thread segment.

19. The self-tapping implant of claim 18 wherein the threaded surface of said body is tapered in the longitudinal direction along at least a portion of said recesses so that successive cutting edges along the thread in the tapered region have progressively changing radii.

20. The self-tapping implant of claim 19 wherein both the minor and major radii of the modified thread segments between said recesses follow said longitudinal taper.

21. The self-tapping implant of claim 20 wherein said minor radius tapers further than said major radius.

22. The self-tapping implant of claim 18 wherein each of said plurality of recesses extends in a direction parallel to a longitudinal axis of said body.

23. The self-tapping implant of claim 18 wherein each of said recesses extends through one end of the implant.

24. The self-tapping implant of claim 18 wherein said recesses are spaced slightly from the apical end of the implant.

25. The self-tapping implant of claim 18 wherein said recesses are spaced symmetrically around the longitudinal axis of the implant.

26. The self-tapping implant of claim 18 wherein the recess wall that forms each cutting edge extends inwardly from the cutting edge at an acute angle relative to the outer surface of the implant contiguous to the cutting edge.

27. The self-tapping implant of claim 18 wherein the recess wall that forms each cutting edge extends longitudinally through the thread at an acute angle relative to the spiral path of the thread.

28. The self-tapping implant of claim 18 wherein the radius of curvature of each of said modified thread segments is smaller than the radius of curvature of the wall of said preformed hole in the bone.

29. The self-tapping implant of claim 18 which is made of titanium.

30. The self-tapping implant of claim 18 wherein said body further includes means for coupling a prosthesis thereto.

31. The self tapping implant of claim 30 wherein said coupling means includes an internal bore in said body.

32. The self-tapping implant of claim 30 wherein said coupling means is located at an end opposite said first end.

33. A self-tapping implant for installation in living bone and to which a prosthesis is to be coupled comprising:

a generally cylindrical body having a threaded outer surface for securing the implant to the walls of a preformed hole in said living bone, said body including means for coupling said prosthesis thereto, said body having a plurality of longitudinal recesses formed in said threaded surface and extending longitudinally through a plurality of turns of the thread to form a plurality of modified thread segments each having a pitch radius measured from said longitudinal axis of said body, each of said plurality of modified thread segments having a lead end with a self-tapping cutting edge and a trailing end, said pitch radii of said modified thread segments diminishing from said lead end to said trailing end.

34. The self-tapping implant of claim 33 wherein said threaded outer surface of said body is tapered in the longitudinal direction along at least a portion of said recesses, successive ones of said cutting edges in the tapered region have progressively changing radii.

35. The self-tapping implant of claim 33 wherein both the minor and major radii of said modified thread segments diminish following said cutting edge.

36. The self-tapping implant of claim 35 wherein said minor radius diminishes further than said major radius.

37. The self-tapping implant of claim 33 wherein each of said recesses extends through one end of the implant.

38. The self-tapping implant of claim 33 wherein said pitch radii diminish immediately behind said cutting edges.

39. A self-tapping implant for forming internal threads in a bore within living bone for receiving said implant, said implant comprising:

a generally cylindrical body having a threaded outer surface for securing the implant to said bore, said body having a tapered threaded end portion with a plurality of cutting edges alternating with modified thread segments, said modified thread segments having relief means following said cutting edges for displacing the major and minor radial dimension of said modified thread segment inwardly away from a confronting surface of said bore when said implant is inserted into said bore.

40. The self-tapping implant of claim 39 wherein said relief means occurs immediately behind said cutting edges.

41. The self-tapping implant of claim 39 wherein said main body further includes recesses extending through said tapered threaded end portion and through an apical end of said body of said implant.

42. The self-tapping implant of claim 39 wherein the radius of curvature of each of said modified thread segments is smaller than a radius of curvature of the wall of said bore in the bone.

43. The self-tapping implant of claim 39 wherein said implant is made of titanium.

44. The self-tapping implant of claim 39 wherein said modified thread segments include a major radius and a minor radius, said relief means including said major and minor radii maintaining a constant dimension around an axis that is offset from a longitudinal axis of said body.

45. The self-tapping implant of claim 39 wherein said body further includes means for coupling a prosthesis thereto.

46. The self-tapping implant of claim 45 wherein said coupling means includes an internal bore in said body.

47. The self-tapping implant of claim 45 wherein said coupling means is located at an end opposite said tapered threaded end portion.

48. The self-tapping implant of claim 39 wherein said minor radius diminishes by an amount to at least offset the decrease in trough area between threads of said threaded surface associated with said tapered region.

49. The self-tapping dental implant of claim 48 wherein said minor radii diminish further than said major radii.

50. The self-tapping dental implant of claim 48 wherein said coupling means includes an internal bore within said body.

51. The self-tapping dental implant of claim 50 wherein said coupling means further includes a manipulating fitting.

52. The self-tapping dental implant of claim 50 wherein said major and minor radii of each of said modified thread segments diminish.

53. The self-tapping dental implant of claim 48 wherein said minor radius diminishes by an mount to at least offset the decrease in trough area between threads of said threaded surface associated with said tapered region.

54. A self-tapping implant for installation in living bone comprising:

a generally cylindrical body having tapered lower portion near a lower end and a threaded outer surface for securing the implant to the walls of a preformed hole in said living bone, said body having a plurality of longitudinal recesses formed in said threaded surface and extending longitudinally through a plurality of turns of the thread within said lower portion to form a plurality of modified thread segments, each of said plurality of modified thread segments having a lead end with a self-tapping cutting edge and a trailing end, and two vertically adjacent modified thread segments along said lower portion defining a trough therebetween having a trough radius, said trough radius decreasing from said lead end to said trailing end by an amount to at least offset the increase in pitch radius of said modified thread segments due to the tapering of said lower portion.

55. The self-tapping implant of claim 54 wherein said body further includes means for coupling a prosthesis thereto.

56. The self-tapping implant of claim 55 wherein said coupling means includes an internal bore in said body.

57. The self-tapping implant of claim 55 wherein said coupling means is located at an upper end of said body.

58. A self-tapping dental implant for installation in living bone comprising:

a generally cylindrical body having a longitudinal axis and a threaded outer surface for securing the implant to the walls of a preformed hole in said living bone, said body having a plurality of longitudinal recesses formed in said threaded surface and extending longitudinally through a plurality of turns of the thread to form a plurality of modified thread segments each having a pitch radius measured from said longitudinal axis of said body, each of said plurality of modified thread segments having a lead end with a self-tapping cutting edge and a trailing end, said pitch radii of said modified thread segments diminishing from said lead end to said trailing end.

59. The self-tapping dental implant of claim 58 wherein said threaded outer surface of said body is tapered in the longitudinal direction along at least a portion of said recesses, successive ones of said cutting edges in the tapered region have progressively changing radii.

60. The self-tapping dental implant of claim 58 wherein both the minor and major radii of said modified thread segments diminish following said cutting edge.

61. The self-tapping dental implant of claim 58 wherein each of said recesses extends through one end of the implant.

62. The self-tapping dental implant of claim 58 wherein said pitch radii diminish immediately behind said cutting edges.

63. The self-tapping dental implant of claim 47 wherein said minor radius diminishes further than said major radius.

64. A self-tapping implant for installation in living jawbone and for use as an anchor for a dental component, comprising:

a generally cylindrical body having an apical end, a gingival end, and a thread making multiple turns around said body between said ends to form a threaded outer surface, said threaded surface tapering inwardly toward a longitudinal axis of said cylindrical body from a point above said apical end to said apical end;

means for coupling said body to said dental component;

a self-tapping region on said threaded outer surface for developing internal threads in said jawbone, said self tapping region including a sequence of cutting edges each of which having therebehind a modified segment of said thread, said modified thread segment having a minor and major radii measured with respect to said longitudinal axis, said major and minor radii of a plurality of said modified thread segments decreasing in a circumferential direction away from said cutting edge.

65. The self-tapping dental implant of claim 64 wherein said major radii diminish immediately behind said cutting edges.

66. The self-tapping dental implant of claim 64 wherein said minor radii diminish immediately behind said cutting edges.

67. The self-tapping dental implant of claim 64 wherein each of said recesses has a major dimension in the longitudinal direction.

68. An implant intended for installation in a component of the human body, comprising:

a generally cylindrical body having an lower end, an upper end, and a thread making multiple turns around a longitudinal axis of said body between said ends to form a threaded outer surface of said body; and a self-tapping region on said threaded outer surface for developing internal threads in said component, said self tapping region including a sequence of cutting edges each of which having therebehind a modified segment of said thread, said modified thread segment having a minor and major radii measured with respect to said longitudinal axis, said major and minor radii of a plurality of said modified thread segments decreasing in a circumferential direction away from said cutting edge.

69. The implant of claim 68 wherein said body further includes means for coupling a prosthesis thereto.

70. The implant of claim 69 wherein said coupling means includes an internal bore within said body.

71. The implant of claim 70 wherein said internal bore is centered on said longitudinal axis of said body.

72. The implant of claim 68 wherein said minor radius diminishes by an amount to at least offset the decrease in trough area between threads of said threaded surface associated with said tapered region.

* * * * *

UNITED STATES PATENT AND TRADEMARK OFFICE
CERTIFICATE OF CORRECTION

PATENT NO. : 5,727,943
DATED : March 17, 1998
INVENTOR(S) : Beaty et al.

It is certified that error appears in the above-identified patent and that said Letters Patent is hereby corrected as shown below:

Column 8, Claim 11, line 56, delete "bone" and insert --bore--.

Signed and Sealed this

Eighth Day of September, 1998

*Attest:*

BRUCE LEHMAN

*Attesting Officer*          *Commissioner of Patents and Trademarks*